United States Patent [19]

Vacek

[11] 4,319,046

[45] Mar. 9, 1982

[54] PREPARATION OF 1,2 DIAMINOBENZENE BY HIGH PRESSURE ACID HYDROLYSIS OF BENZEMIDAZOLONE

[75] Inventor: Lubomir Vacek, Toledo, Ohio

[73] Assignee: The Sherwin-Williams Company, Cleveland, Ohio

[21] Appl. No.: 946,284

[22] Filed: Sep. 27, 1978

Related U.S. Application Data

[63] Continuation of Ser. No. 818,173, Jul. 22, 1977, abandoned.

[51] Int. Cl.$^3$ .............................................. C07C 85/20
[52] U.S. Cl. .................................... 564/413; 548/305
[58] Field of Search ............... 260/578, 582; 548/305; 564/413

[56] References Cited

U.S. PATENT DOCUMENTS

| | | | |
|---|---|---|---|
| 3,128,310 | 4/1964 | Koch | 260/582 |
| 3,414,619 | 12/1968 | Cross et al. | 260/582 |
| 3,441,586 | 4/1969 | Luberoff et al. | 260/582 X |
| 3,620,929 | 11/1971 | Kober et al. | 548/305 X |

FOREIGN PATENT DOCUMENTS

795639  5/1958  United Kingdom ............... 260/582

OTHER PUBLICATIONS

Wertheim, "Organic Chemistry", Third Edition, pp. 309–310 (1951).
Hackh's Chemical Dictionary, Fourth Edition, p. 87 (1972).
Sawlewicz et al., "Roczniki Chemii Ann. Soc. Chim. Polonorum", vol. 38, pp. 1073–1078 (1964).
Israel et al., "J. Heterocyclic Chem.", vol. 8, pp. 1015–1018 (1971).
Harple et al., "Analytical Chem.", vol. 42, pp. 1658–1659 (1970).
Rossi et al., "Helv. Chem. Acta", vol. 43, pp. 1046–1056 (1960).
Popov et al., "Chem. Ab.", vol. 85, Ab. No. 46503z (1976).
Sawlewicz et al., "Chem. Ab.", vol. 62, Ab. No. 6473h (1965).

*Primary Examiner*—John Doll
*Attorney, Agent, or Firm*—James V. Tura; Robert E. McDonald

[57] ABSTRACT

This invention is directed to a process for preparing 1,2-diaminobenzene which comprises acid hydrolyzing 2-benzimidazolone in an aqueous medium at elevated temperatures and pressures.

12 Claims, No Drawings

PREPARATION OF 1,2 DIAMINOBENZENE BY HIGH PRESSURE ACID HYDROLYSIS OF BENZEMIDAZOLONE

This is a continuation of application Ser. No. 818,173, filed July 22, 1977, now abandoned.

This invention relates to a process for preparing 1,2-diaminobenzene which comprises hydrolyzing 2-benzimidazolone in an acidic medium at increased temperatures and pressures. More specifically, the reaction takes place at temperatures ranging above 190° C. and under pressures above atmospheric pressure.

Presently, 1,2-diaminobenzene is prepared by the catalytic reduction of 2-nitroaniline. While the yields of the diamine from the reduction of 2-nitroaniline are good, the use of nitroaniline, however, has at least two drawbacks. First, since nitroaniline is a by-product, the availability of the compound is limited and second the toxicity status of nitroaniline is still in question, see U.S. Pat. Nos. 2,956,082 and 3,230,259.

To avoid these and other problems encountered heretofore, the process of preparing diaminobenzene in accordance with this invention comprises starting with an intermediate which is readily available. Specifically, in accordance with this invention, the diaminobenzene is derived directly from 2-benzimidazolone. The benzimidazolone preferably is obtained by a process initially utilizing commercially available isatoic anhydride. More specifically, the 2-benzimidazolone is obtained by reacting 2'-carbamoylphthalanilic acid in a liquid alkaline medium in the presence of a metal hypohalite, e.g. sodium hypochlorite over a wide range of temperatures. The 2'-carbamoylphthalanilic acid is obtained from two reactions starting with isatoic anhydride. The details of preparing 2-benzimidazolone starting with isatoic anhydride is specifically set forth in copending application titled Process for Preparing 2-Benzimidazolone by Duane A. Heyman, Ser. No. 818,172; filed on July 22, 1977, now abandoned the disclosure of which is hereby incorporated by reference.

Although the copending application discloses a preferred process for preparing 2-benzimidazolone, it is obvious that other methods may be used to obtain this compound which can be then converted to 1,2-diaminobenzene in accordance with this invention. Accordingly, it is an object of this invention to provide a process for preparing 1,2-diaminobenzene from 2-benzimidazolone and preferably from 2-benzimidazolone derived from a series of reactions initially starting with isatoic anhydride.

The process of this invention comprises the acid hydrolysis of 2-benzimidazolone at increased temperatures and pressures. Generally, 2-benzimidazolone has been considered to be resistant to acid hydrolysis as appropriate derivatives have shown no apparent reaction at temperatures ranging up to 180° C., see Rossi et al, Helv. Chem., Acta, 43, 1046 (1960); Israel et al, Journal of Heterocyclic Chem., 8, 1015 (1971) and Harple et al, Analytical Chem., 42, 1658 (1970).

Contrary to the general belief, however, it has been found in accordance with this invention, that 2-benzimidazolone is readily hydrolyzed in an aqueous acidic medium over a range of acid concentrations and at temperatures in excess of about 190° C. The reaction may be carried out at temperatures as high as 310° C. over a comparatively short time period, e.g. periods of about a half-hour or more and under pressures above atmospheric pressure. More particularly, in accordance with this invention, 2-benzimiazolone is hydrolyzed in an aqueous medium in the presence of at least one mineral acid at temperatures ranging from about 190° C. to 310° C. and preferably at temperatures ranging from about 225° C. to 275° C.

The reaction takes place under pressures ranging above atmospheric, i.e. ranging from about 15 psi to 1500 psi or higher and more likely at pressures above 100 psi, e.g. from 400 to 1000 psi. The mineral acid used in the hydrolysis includes at least one acid such as hydrochloric acid, sulfuric acid, nitric acid or any combination thereof over a wide range of acid concentrations.

The acid concentration in the reaction may range from as low as about 0.1 normal up to about 24 normal or higher depending on the type of acid used and more likely may range from 1.0 to 12 normal in the case of a monoprotic acid. As the following Table I shows, the hydrolytic process is evident even by the action of such weak acids as water, but, if a high yield of the 1,2-diaminobenzene is desired in a practical length of time of the hydrolytic process and at a practical temperature, a strong acid, preferentially a mineral acid, in an amount of at least two equivalents per mole of 2-benzimidazolone should be used.

The reaction proceeds for a time period ranging from at least about one-half hour up to eight hours or more to give very good yields of the 1,2-diaminobenzene. The reaction may be illustrated by the following equation:

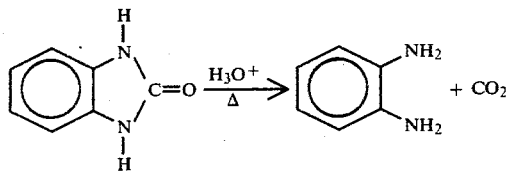

The data in Table I illustrates the various conditions under which the 1,2-diaminobenzene may be obtained in accordance with this invention.

TABLE I

| ACID HYDROLYSIS OF 2-BENZIMIDAZOLONE[a] | | | |
|---|---|---|---|
| Time (Hr.) | Temp (°C.) | Molarity Acid | % Crude Diamine[c] |
| 1 | 195 | 12 | 1 |
| 2 | 255 | 6 | 98 |
| 2 | 255 | 1.2 | 50 |
| 1 | 250 | 9[b] | 85 |
| 1 | 273 | 4.8 | 90 |
| 3.5 | 305 | 0[d] | 4 |

[a]The reactions were completed with 1.0 g of 2-benzimidazolone in 10-20 ml of aqueous hydrochloric acid.
[b]Sulfuric acid.
[c]Recovered yields of 1,2-diaminobenzene with the remaining materials generally being unreacted 2-benzimidazolone.
[d]No added acid. Water as solvent.

The following example specifically illustrates the process for hydrolyzing 2-benzimidazolone to obtain 1,2-diaminobenzene.

EXAMPLE 1

ACID HYDROLYSIS OF 2-BENZIMIDAZOLONE

Recrystallized 2-benzimidazolone, 1.0 g (0.0075 mole), 6 ml of distilled water and 4 ml of concentrated hydrochloric acid were charged into a 200 mm pyrex test tube. The tube, containing an off-white suspension, was cooled with dry ice, sealed with an oxygen torch and placed in a bomb reactor along with methanol (heat transfer and pressure equalization agent). The sealed bomb was placed in an oil bath and heated to 265° C. (two hours to reach temperature). The bath was held at 265°±5° C. for two hours and then cooled to room temperature. Upon opening the bomb the sealed glass tube was found to contain a dark green reaction mixture. The tube was cooled with dry ice and carefully opened. (The tube is under pressure with a potential for shattering!) The contents of the tube were washed into a beaker, cooled with an ice bath, neutralized to pH 7 with 50% aqueous sodium hydroxide, filtered, washed with water, air dried and oven dried about 18 hours at 50° to 60° C. The filtrate was extracted with five portions (25 to 30 ml each) of methylene chloride and then the extracts were reduced to dryness on a rotary film evaporator. A total of 0.85 g (100% yield) of tan-purple solid was collected and identified by an infrared spectrum as being crude 1,2-diaminobenzene. In addition to the above example, the time, temperature, pressure and acid concentrations of the reaction may be varied as illustrated by the data in Table I to obtain 1,2-diaminobenzene.

The 1,2-diaminobenzene or phenylene diamine is generally known to be useful as an intermediate for the preparation of various heterocyclic compounds including, for example, the benzimidazoles and benzotriazoles. These heterocyclic compounds have a variety of uses well known in the art and are particularly useful for the preparation of drugs, see R. C. Elderfield, Heterocyclic Compounds, Wiley, New York, (1957), Vol. 5, pages 274–288. In the case of triazoles, they are especially useful as corrosion inhibitors, see E. B. Miller et al, U.S. Pat. No. 2,861,078; J. W. Long, U.S. Pat. No. 3,564,001.

While this invention has been described by a number of specific embodiments, it is obvious there are variations and modifications which can be made without departing from the spirit and scope of the invention as set forth in the appended claims.

The invention claimed is:

1. A process for preparing 1,2-diaminobenzene which comprises hydrolyzing 2-benzimidazolone in an acidic aqueous medium at temperatures above 190° C. and under pressures above atmospheric pressure to form the diaminobenzene.

2. The process of claim 1 further characterized in that the aqueous medium comprises at least two equivalents of mineral acid, for each mole of 2-benzimidazolone.

3. The process of claim 2 further characterized in that at least one of the mineral acids is hydrochloric acid, sulfuric acid or nitric acid.

4. The process of claim 1 further characterized in that the acid hydrolysis takes place at temperatures ranging up to about 300° C.

5. The process of claim 1 further characterized in that the acid hydrolysis takes place at temperatures ranging from about 225° C. to 275° C. under pressures ranging up to about 1500 psi.

6. The process of claim 1 further characterized in that the acidic aqueous medium is 0.1 to 24 normal.

7. The process of claim 6 further characterized in that the acidic aqueous medium comprises hydrochloric acid and the normality ranges from 1.0 to 12.

8. A process for preparing 1,2-diaminobenzene which comprises acid hydrolyzing 2-benzimidazolone in a mineral acid aqueous medium having an acid normality ranging from 0.1 to 24 normal at temperatures ranging from 190° C. to 310° C. and under pressures above atmospheric pressure to form the diaminobenzene.

9. The process of claim 8 further characterized in that the pressure ranges from above atmospheric pressure to about 1500 psi.

10. The process of claim 8 further characterized in that the acid is hydrochloric acid.

11. The process of claim 8 further characterized in that the mineral acid is sulfuric acid.

12. The process of claim 2 further characterized in that the mineral acid is sulfuric acid.

* * * * *